(12) United States Patent
Stanfield

(10) Patent No.: US 11,961,415 B2
(45) Date of Patent: Apr. 16, 2024

(54) TRAINING APPARATUS AND METHODS FOR MEDICAL DIAGNOSTIC AND TREATMENT

(71) Applicant: Sula Stanfield, Houston, TX (US)

(72) Inventor: Sula Stanfield, Houston, TX (US)

(73) Assignee: Sula Stanfield, Houston, TX (US)

( * ) Notice: Subject to any disclaimer, the term of this patent is extended or adjusted under 35 U.S.C. 154(b) by 45 days.

(21) Appl. No.: 17/942,934

(22) Filed: Sep. 12, 2022

(65) Prior Publication Data
US 2023/0222941 A1   Jul. 13, 2023

Related U.S. Application Data

(60) Provisional application No. 63/298,207, filed on Jan. 10, 2022.

(51) Int. Cl.
*G09B 23/28* (2006.01)
*A61M 1/28* (2006.01)
*A61M 1/36* (2006.01)

(52) U.S. Cl.
CPC .......... *G09B 23/285* (2013.01); *A61M 1/285* (2013.01); *A61M 1/3655* (2013.01)

(58) Field of Classification Search
CPC ....... G09B 23/28; G09B 23/30; G09B 23/303
See application file for complete search history.

(56) References Cited

U.S. PATENT DOCUMENTS

| | | | | |
|---|---|---|---|---|
| 11,466,235 B2* | 10/2022 | Bluemler | ................ | C11D 3/48 |
| 2006/0064159 A1* | 3/2006 | Porter | ................ | A61M 1/3655 |
| | | | | 623/1.24 |
| 2006/0223039 A1* | 10/2006 | Williams | ................ | G09B 23/28 |
| | | | | 434/262 |
| 2012/0034587 A1* | 2/2012 | Toly | ................ | G09B 23/30 |
| | | | | 434/267 |
| 2014/0205981 A1* | 7/2014 | Ryder | ................ | G09B 7/06 |
| | | | | 434/262 |
| 2015/0004584 A1* | 1/2015 | Galibois | ................ | G09B 23/303 |
| | | | | 434/270 |
| 2017/0229044 A1* | 8/2017 | Benson | ................ | G09B 23/285 |
| 2023/0390467 A1* | 12/2023 | Ghahramani | ................ | G16H 20/17 |

FOREIGN PATENT DOCUMENTS

JP   2017198938 A   * 11/2017
JP   2020034833 A   *  3/2020

* cited by examiner

*Primary Examiner* — Kurt Fernstrom
(74) *Attorney, Agent, or Firm* — Bela Malik; Affordable Patent Agency, LLC

(57) ABSTRACT

This application relates to a system, apparatus, and methods for renal dialysis training the patients, providers, and caretakers without harming or injuring an actual patient. The renal dialysis may be hemodialysis, peritoneal dialysis, or both. The system comprises at least one closed-loop apparatus with at least one of the following—artificial blood, cannulatable vascular system, heart, peritoneal membrane and cavity, vascular valves, artificial skin, and/or other artificial organs set inside a mannequin, humanoid, or any human-like machine. The artificial organ in the mannequin can be accessed through an opening in the chest, arm, abdominal cavity, thigh, groin, neck, and any combination thereof. The renal dialysis may be through catheter access, arterio-venous graft access, and peritoneal catheter access.

25 Claims, 5 Drawing Sheets

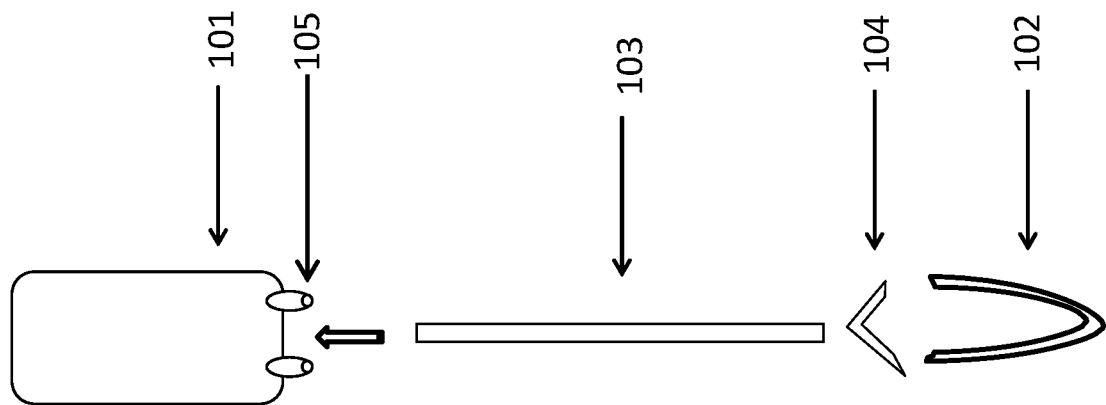
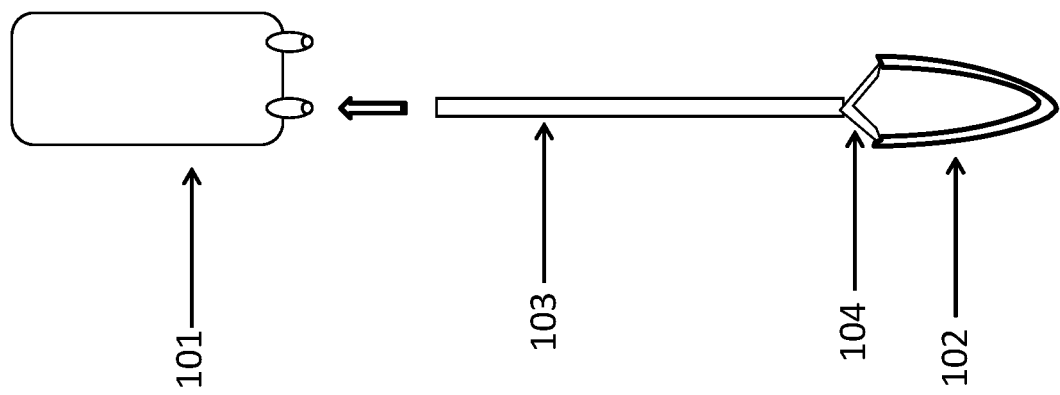
Fig. 1

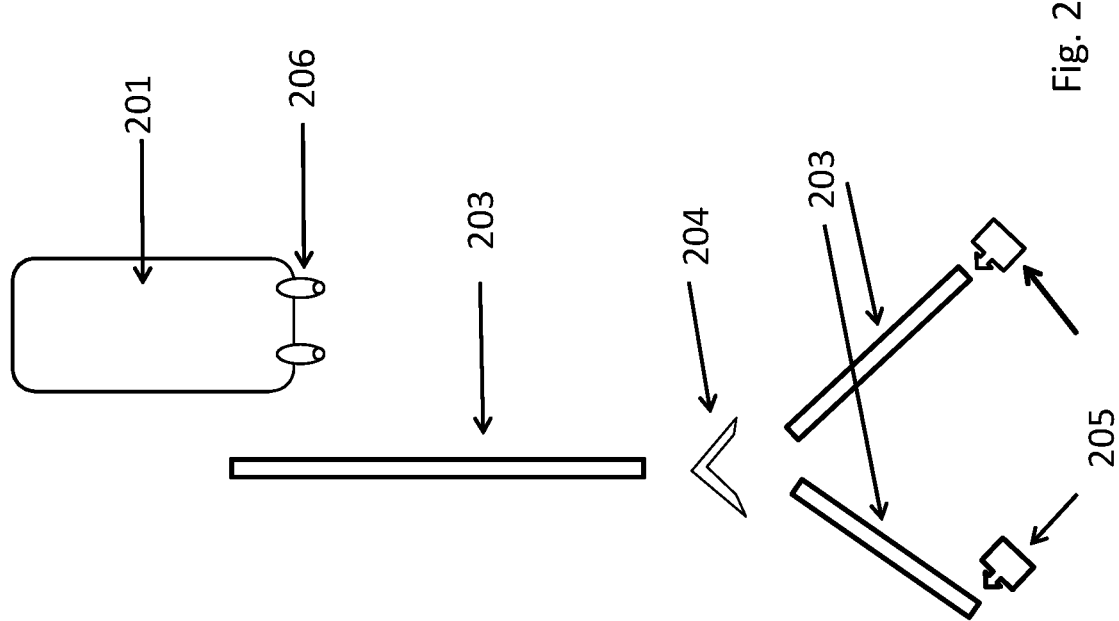
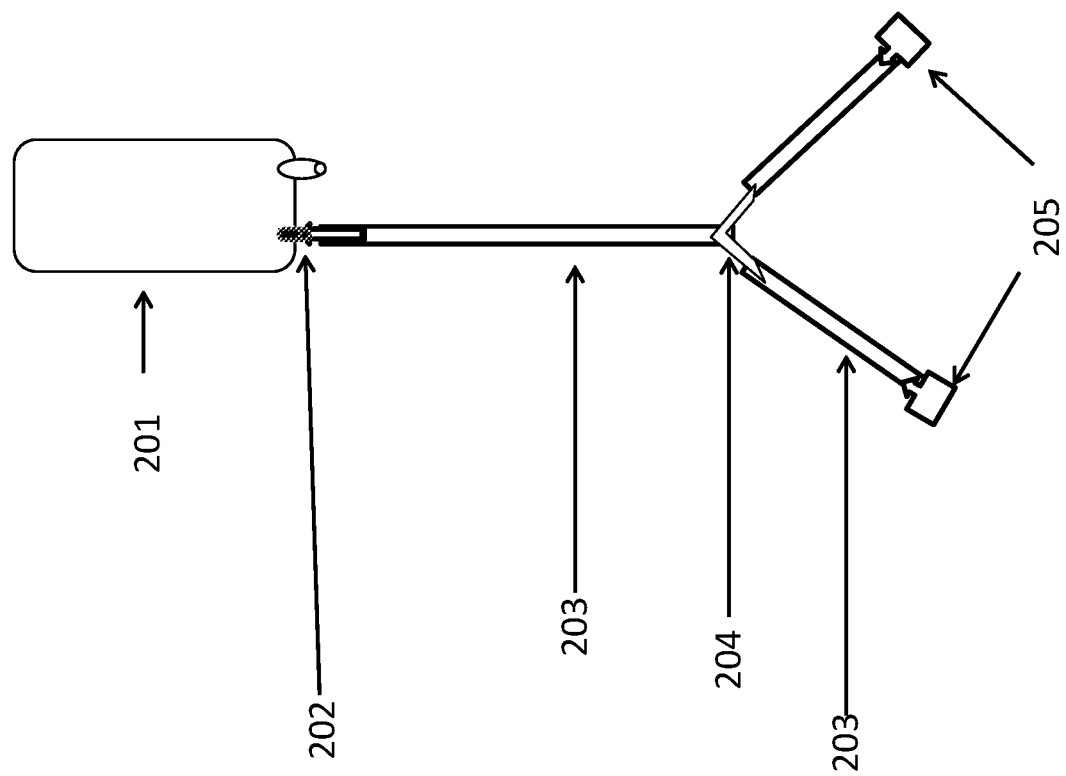
Fig. 2

TRAINING APPARATUS AND METHODS FOR MEDICAL DIAGNOSTIC AND TREATMENT

CROSS-REFERENCE TO RELATED APPLICATIONS

None
This nonprovisional application claims benefit to previously filed provisional application No. 63/298,207, filed on 10 Jan. 2022.

STATEMENT REGARDING FEDERALLY SPONSORED RESEARCH OR DEVELOPMENT

Not applicable.
The present disclosure relates to a renal dialysis training apparatus for training providers, users, and patients.

BACKGROUND

Kidneys play a vital role in maintaining normal blood pressure and electrolyte balance. Therefore, kidney failure results in an imbalance in total body electrolytes and blood pressure. There are two types of severe kidney failure—the first is acute, which is caused by low blood pressure, urinary tract blockage, muscle wasting, hemolytic uremic disease, and certain medications or chronic kidney failure. The second is chronic and is caused by chronic kidney failure, including diabetes, high blood pressure, nephrotic syndrome, and polycystic kidney disease.

The nephron is a functional kidney unit made of a filtering unit, glomerulus, and renal tubules. Glomerulus filters out toxic waste materials from the blood, and one such waste is creatinine, which is neither absorbed nor secreted in the renal tubules. Therefore, comparative blood and urine creatinine levels are a good measure of the glomerular and, by extension, kidney function. Glomerular filtration rate (GFR) is used to assess the excretory function of the kidneys and the Staging of kidney failure. Diagnosis of kidney failure is based on a GFR of less than 15 is stage 5 chronic kidney disease (also called End-Stage Kidney Disease or ESKD). The only treatment for acute and chronic kidney failure is renal replacement therapy, which is dialysis or kidney transplantation.

BRIEF DESCRIPTION OF THE INVENTION

This application relates to a system, apparatus, and method for training the patients, providers, and caretakers in performing diagnostic and treatment, such as, but not limited to, renal dialysis at home, in an educational institute, or in any clinical setting. Renal dialysis is a process performed as renal replacement therapy in patients with end-stage kidney disease. In these patients, kidney function is lost, so a machine is used to perform the filtration part of the kidney function. There are two main types of dialysis, namely, hemodialysis and peritoneal dialysis, and they both remove wastes and excess water from the blood, but in different ways. The disclosure herein may be used to train users with at least one or both types of dialysis. The apparatus and methods may provide the users with the most realistic experience, therefore, practical and best training.

The system comprises at least one closed-loop apparatus with at least one blood mimicking fluid (artificial blood), tubing simulating the vascular system (artificial vascular system), a bag simulating the heart (artificial heart), a bag simulating peritoneal cavity (artificial peritoneal cavity), other artificial organs, and clips mimicking vascular valves (artificial valves) set inside a mannequin, dummy, humanoid, or any human-like machine with or without artificial skin.

The system and apparatus of the disclosure may be closed entirely with no compartments or part of the apparatus that may be open, i.e., all biological systems and organs being simulated herein may be closed.

In an embodiment, a training apparatus comprises at least one artificial organ system within a mannequin. The artificial organ system forms a closed-loop structure, and the artificial organ system is configured to be cannulated from outside at at least one location on the mannequin, and the apparatus is configured for renal dialysis.

In an embodiment, the artificial organ system may be cannulated in the thigh, upper, middle, lower arm, and any combination thereof.

A patient's blood supply during hemodialysis may be accessed through three primary accesses-points and methods: an intravenous catheter, an arteriovenous fistula (AV), and a synthetic graft. A patient may, at any given time, have one or more access points. Hemodialysis may be a dialysis process that may be carried out by accessing the vascular system.

In an embodiment, the apparatus has at least one access point, e.g., an intravenous catheter, an arteriovenous fistula, and a synthetic graft. An arteriovenous fistula is a native artery tied to a native vein, the patient's own vein and artery. On the other hand, a synthetic graft is an artificial material connected to an artery and a vein to create a pathway for performing dialysis.

The system and apparatus may be used to teach a trainee, such as but not limited to, a caretaker and providers, to perform clinical diagnostic tests and/or treatment. For instant, but not limited to performing dialysis, obtaining blood cultures, drawing blood specimens, intravenous infusions, administering blood transfusions, administering intravenous medications, etc., or any combination thereof.

The disclosure herein relates to an apparatus for training the patients, providers, and caretakers in performing medical treatment(s) and diagnostic test(s) at home, in educational, or in clinical settings. The system comprises at least one closed-loop apparatus and further comprises at least one artificial blood, an artificial vascular system (tubing), an artificial heart, an artificial peritoneal cavity, artificial vascular valves, artificial skin, or another artificial human organ set inside a mannequin, humanoid, or human-like machine (mannequin).

In an embodiment, the artificial organ is a cardiovascular system further connected to a hemodialysis catheter that may have two ports and may be clamped when not in use and open when in use. The two catheter ports, an arterial port may be indicated by a red clamp carrying blood from the heart, and a venous port may be indicated by a blue clamp returning blood to the heart.

The apparatus may be a closed system receiving and returning simulated blood through the self-contained system.

In an embodiment, the artificial organ is a cardiovascular system, and the cardiovascular system is connected to an arteriovenous fistula configured to be renal dialyzed through the arteriovenous fistula.

In an embodiment, the artificial organ is a peritoneal cavity connected to a peritoneal dialysis catheter port.

In an embodiment, the dialysis is through a peritoneal cavity, wherein the peritoneal cavity is connected to a renal dialyzing machine.

In an embodiment, renal dialysis is a continuous cyclic peritoneal dialysis.

In an embodiment, renal dialysis is a continuous ambulatory peritoneal dialysis.

In an embodiment, the cannulatable location is self-sealing.

In an embodiment, the artificial organ is a cardiovascular system or a peritoneal cavity, wherein the cardiovascular system and peritoneal cavity comprise natural rubber and silicone.

In an embodiment, the cardiovascular system and peritoneal cavity comprise individual flexible bags. Therefore, each artificial system corresponds to a separate and individual bag without needing a central hard-material tank or container.

In an embodiment, the artificial organ in the mannequin can be accessed through the opening in the chest, arm, abdominal cavity, thigh, groin, neck, and any combination thereof. In the real world, access to the patient's heart and peritoneal cavity may be gained through an external catheter similar to the disclosure herein.

In an embodiment, the mannequin's height is 39 to 42 inches, shoulder to shoulder width of 16 to 22 inches, the depth of 10 to 7 inches, and the weight of 5.4 pounds (lbs) to 7.6 lbs In an embodiment, the closed-loop structure is air-tight without any trapped air pockets.

In an embodiment, the closed system with collapsible bags may decrease the chance of air entering the system, reducing the probability of trapped air pockets.

In an embodiment, the closed system makes the apparatus, tubing, and bags mishandling-proof, leak-proof, or both.

In an embodiment, the closed-loop structure is connected to a liquid leak-sensing alarm system.

In an embodiment, the closed-loop structure is connected to an automatic shut-off system.

In an embodiment, the mannequin's limbs, head, torso, and artificial organs are detachable and attachable.

In an embodiment, the cannulating needle may be in size from 14 to 17 gauge. For example, 14, 15, 16, 17, and any combination thereof.

In an embodiment, renal dialyzing is infection detecting.

In an embodiment, the method of use for training on a renal dialyzing apparatus comprising at least one closed-loop artificial organ system within a cannulatable mannequin, and the method comprises of setting upright the mannequin, attaching a secondary intravenous mimicking tubing to a heart-mimicking bag filled with blood mimicking solution without air-pockets, connecting the heart to a hemodialysis catheter port or an artificial arterio-venous graft barbed Y-connector.

In an embodiment, a blood leak detecting system connected to the artificial organ system can shut off renal dialyzing.

In an embodiment, the peritoneal mimicking bag connecting to a peritoneal dialysis catheter port connects to an automated peritoneal dialysis machine capable of performing multiple renal dialysis exchanges.

In an embodiment, the peritoneal dialysis tubing has a clamp to prevent leakage when connecting and disconnecting from peritoneal dialysis machine.

In an embodiment, the bag(s) may be drained by simply removing the caps from the catheter or disconnecting the AVG tubing from one end of the barbed connector. After drainage, the caps may be replaced and AVG re-attached. The draining may be facilitated by tilting the mannequin from side to side or by placing the mannequin in a Trendelenburg position.

It is critical in healthcare to cause no harm to a patient. The apparatus, system, and methods disclosed herein may prevent or avoid unnecessary pain and injury to patients suffering from various diseases, such as but not limited to kidney failure, who need renal dialysis, from being harmed as a result of untrained dialysis personnel. Caretakers, providers, and patients may be trained to acquire specialized skills without using a human patient for the best and safest outcome. This disclosure's apparatus, system, and methods may mimic the real-world environment and allow the trainees to make mistakes without any pain, injury, or harm to an actual patient. The disclosure may provide flexibility in training a multitude of individuals, such as but not limited to providers, caretakers, patients themselves, etc., to learn how to perform dialysis in a non-clinical setting without the use of actual human patients. The apparatus, system, and methods disclosed herein may be realistic, user-friendly, and highly functional.

BRIEF DESCRIPTION OF THE FIGURES

FIG. 1: Shown here is an example of a simulated heart with blood vessels connected to a simulated artificial arterio-venous graft AV graft.

FIG. 2: Simulated heart with blood vessel connected to simulated or artificial dialysis catheter.

DETAILED DESCRIPTION OF THE INVENTION

Figure 3:
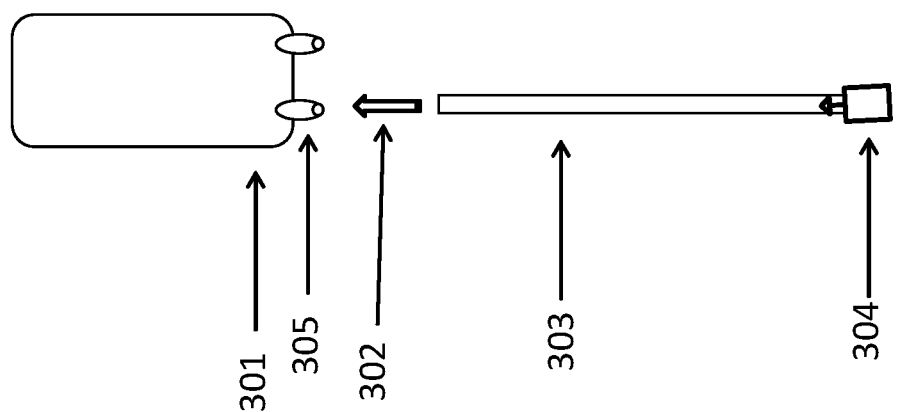
FIG. 3: Shown here is a simulated or artificial peritoneal cavity and catheter.

Examples of embodiments are provided so that this disclosure will be thorough and will fully convey the scope to those who are skilled in the art. Numerous specific details are set forth, such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components but do not preclude the presence or addition of one or more other features, integers, steps, operations, elements, components, and/or groups thereof. The method steps, processes, and operations described herein are not to be construed as necessarily requiring their performance in the particular order discussed or illustrated unless specifically identified as an order of performance. It is also to be understood that additional or alternative steps may be employed.

The preceding summary, as well as the following detailed description of certain embodiments, will be better understood when read in conjunction with the appended figure of experimental data and results. As used herein, an element or step recited in the singular and proceeded with the word "a" or "an" should be understood as not excluding the plural of said elements or steps unless such exclusion is explicitly stated. Furthermore, references to "one embodiment" or "an embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. When a definition is provided herein, it supersedes any other meaning or definition.

As used herein, the term "mannequin" means any human-looking, human-like, humanoid, or human mimicking apparatus, device, or machine.

As used herein, the term "artificial" organ means any device capable of mimicking a human organ or organ system function, structure, or part of the said function, structure, or any combination thereof.

In the United States, acute renal failure affects about 3 per 1,000 people annually, whereas chronic renal failure affects about 1 in 1,000 people annually. Although acute renal failure is often reversible while chronic renal failure often is not, both require dialysis as renal replacement therapy. Nearly 786,000 people in the United States live with ESKD, 71% on dialysis and 29% with a kidney transplant. The projections suggest that by 2030, the number of ESRD patients will increase to approximately 1,259,000. Furthermore, about 12-13% of all dialysis patients perform the dialysis at home. The financial burden of ESKD is enormous-Medicare-related spending for beneficiaries with ESKD was about $ 49.2 billion in 2018.

People will benefit from the disclosure herein because the patients, providers, and caretakers will be better trained to perform a variety of medical treatments and diagnostic tests, for example, but not limited to, performing dialysis, both peritoneal and hemodialysis, obtaining blood cultures, drawing blood specimens, intravenous infusions, administering blood transfusions, administer intravenous medications, blood transfusions skills, intravenous medication administration skills, catheter declot skills, blood culture collection skills, peritoneal culture, cell count and gram stain collection, peritoneal dialysis, catheter flush, central line dressing change, peritoneal dialysis catheter care, sim-lab critical scenario while on dialysis, etc., or any combination thereof.

This application relates to a system, an apparatus, and method for training the patients, providers, and caretakers in performing dialysis, both peritoneal and hemodialysis, obtaining blood cultures, drawing blood specimens, intravenous infusions, administering blood transfusions, administering intravenous medications, blood transfusions skills, intravenous medication administration skills, catheter declot skills, blood culture collection skills, peritoneal culture, cell count and gram stain collection, peritoneal dialysis catheter flush, central line dressing change, peritoneal dialysis catheter care, sim-lab critical scenario while on dialysis, etc., at home, educational, or in any clinical setting. The scenario such as management of air embolism, hypo and hypertension, blood leak, hemolysis, chest pain, cardiac arrest, shortness of breath, first use syndrome, anaphylactic reaction, seizure, dialysis disequilibrium syndrome, flash pulmonary edema. Massive Blood loss, needle dislodgement, electrolytes, peritonitis and hemoperitoneum.

It is critical in healthcare to cause no harm to a patient. The apparatus, system, and methods disclosed herein may prevent patients with kidney failure who need renal dialysis from being harmed due to untrained personnel. Care-takers, providers, and patients may be trained to acquire specialized skills without using a human patient for the best and safest outcome. Because the apparatus, system, and methods of this disclosure may mimic real-world circumstances and the environment; thus, it may allow the trainees to make mistakes without any pain, injury, or harm to actual patients. The disclosure may provide flexibility in training a multitude of individuals, such as but not limited to providers, caretakers, patients themselves, etc., to learn how to perform dialysis in a non-clinical or clinical setting without actual humans. The apparatus, system, and methods disclosed herein may be realistic, user-friendly, and highly functional. The realistic aspect of the disclosure provides a practical, precise, and best user experience.

Besides the pain and discomfort of the procedure, individuals undergoing dialysis are at a greater risk of infections. Therefore, the disclosure herein aims to reduce pain, discomfort, and the possibility of infection and harm by properly and adequately training the dialysis procedure.

The training apparatus and system comprise at least one closed-loop artificial organ and organ system, for example, a cardiovascular system with blood mimicking fluid. The apparatus and system may further include at least one tubing mimicking the vascular system, a non-permeable bag mimicking the heart, clips mimicking vascular valves, etc., set inside a complete or partial mannequin or humanoid.

The system and apparatus of the disclosure may be completely closed with no compartments or part of the apparatus that may be open, i.e., all biological systems and organs being mimicked herein may be closed and not open.

In an embodiment, the closed system makes the apparatus more mobile and portable. Thus, the simulator may be easily moved from station to station without concern for the internal reservoir leaking fluid.

In an embodiment, the tubing may mimic or be an artificial vascular system and bag(s) as an artificial heart, peritoneal cavity, abdominal cavity, etc., and any combination thereof.

In an embodiment, the tubing may act as arterial-venous grafts. Thus, the tube connected to the non-permeable bag, the artificial heart, may carry blood-like liquid away from the artificial heart into the rest of the body, depicting the aorta artery. On the other hand, the tubing that brings liquid back into the artificial heart may depict superior or inferior vena cava or a combination of both. For example, the tubing in a mannequin arm may depict arterial blood supply to the arm, such as the radial or ulnar arteries. These arteries may drain into veins such as the arm's median cubital vein.

The tubing may be self-sealing and may be the tubing that represents the artificial arterio-venous graft (AVG). A graft connects to a vein and artery to facilitate blood flow and allow access to the circulatory system using dialysis. The AVG may be connected to the dialysis machine through dialysis surgical needles to remove blood from the body, circulate it through the dialysis machine, and then return the cleaned blood to the circulatory system. The arterial dialysis surgical needle may be used to carry blood away from the body and through the dialysis machine, and the venous dialysis surgical needle returns the cleaned blood back to the body.

The graft placement may make it easy for the user to replace the graft as needed by simply disconnecting the rubber from the barbed Y-connector and replacing it with a new tubing segment.

In a real-world scenario, no caps may be found on a fistula or graft, but caps may only be found on catheters. Although the placement of the fistula is in the arm, the use of caps may give it the same function as a port coming from the chest, just in a different location.

In an embodiment, the tubing may be attached to a spike.

In an embodiment, the bag may be attached to a spike.

In an embodiment, the bag(s) and tubing may be inserted through the hole in the chest.

In an embodiment, the access points or openings may be in the neck, chest, arm, axilla, abdomen, groin, thigh, etc., and any combination thereof.

In an embodiment, multiple bags may be connected together by a spike connected to 3-inch tubing, which is then connected to a spike in additional bags. This allows for full volume capacity of up to 9 Liters, for example, 1, 2, 3, 4, 5, 5.5, 6, 6.5, 7, 7.5, 8, 8.5 liters and any fraction thereof.

In an embodiment, the simulator may have the capacity of up to 9 L fluid capacity to demonstrate volume overload in the heart, for example, 1, 2, 3, 4, 5, 5.5, 6.5, 7, 7.5, 8, 8.5 Liters.

In an embodiment, the bag attached to the spike and the tubing may be inserted through the hole in the axilla of the mannequin arm, and the tubing may be threaded through the arm, exiting either above or below the elbow on the anterior side of the arm.

In an embodiment, the tubing may be inserted through the hole in the abdomen.

In an embodiment, the mannequin's arm may have at least one hole, for example, one, two, three, or four, for creating and inserting the arterio-venous graft.

In an embodiment, the Arterio-Venous Fistula (AVF) may require inserting large needles into the fistula, which is an acquired skill, and the apparatus of the disclosure teaches such a skill. The gold standard for hemodialysis is the use of an AVF, which requires skills in inserting large needles into the fistula. The apparatus of the disclosure may offer the option for training users on inserting needles into the Arterio-Venous Graft/Arterio-Venous Fistula (AVG/AVF), which may realistically mimic what the user/learner may encounter in the real world.

Additionally, the method is disclosed to ensure the trainee learns skills without causing infections.

The access points may allow each individual to independently use and train with the apparatus and methods of this disclosure. Each individual may use one or more bags mimicking the heart, peritoneal cavity, kidney, etc., without having a central container where all liquids may be contained and/or emptied. This may provide a closed-loop individual training system where individual skills such as catheterization, use of needles, reduced risk of infections, etc., may be monitored. Thus, the inside is not accessible without destroying the integrity of the simulator, which provides for more realistic and individual user customizable apparatus and methods. The system, apparatus, and methods provide multiple training options.

In an embodiment, the apparatus may be a 2-in-1, 3-in-1, or 4-in-1 dialysis simulation, wherein the one apparatus may be used to train in two or more simulations—for example, simulation of peritoneal dialysis and hemodialysis. The hemodialysis may be performed in any one of the three ways—hemodialysis may be accessed through three primary accesses-points and methods: an intravenous catheter, an arteriovenous fistula (AV), and a synthetic graft. The one apparatus simulates all three access and processes of access. Thus, one apparatus may have functionality and structure for one, two, three, or four dialysis simulations.

In an embodiment, the peritoneal dialysis may be through an access point in the belly, which may be beneficial for continuous ambulatory peritoneal dialysis.

In an embodiment, the peritoneal dialysis through the belly may be through a flexible bag since the hard internal case may cause excessive air, which may cause deficiency for use with the peritoneal dialysis cycler machine.

In an embodiment, the peritoneal dialysis machine may deliver continuous cyclic peritoneal dialysis, wherein continuous ambulatory peritoneal dialysis may be a manual setup made up of a bag filled with dialysis solution with tubing attached. The mannequin may be connected directly to the catheter and perform manual fills and drains.

In an embodiment, the peritoneal dialysis may be carried out by using the peritoneal cavity accessed through the abdominal wall.

In an embodiment, the trainee may initiate and complete a dialysis treatment using the mannequin and without using any human patient.

In an embodiment, fluorescence dye(s), colored dyes, microbe-specific sensors, etc., and any combination thereof may be used to detect potential infection or risk of infection.

In an embodiment, the tubing mimicking patients' blood vessels, artificial blood vessels, may be accessed through an external catheter, connecting to a dialysis machine.

In an embodiment, the tubing may be connected to the dialyzing machine, similar to the arm blood vessels in a renal dialysis patient. This forms an artificial organ(s) and dialyzing machine closed-loop system for renal dialyzing patients.

In an embodiment, the apparatus may be closed-loop with the artificial blood vessels and dialyzing machine.

In an embodiment, the apparatus, the system, and/or tubing may be configured to be connected or linked to a catheter through the mannequin's chest wall.

In an embodiment, the apparatus, the system, and/or tubing may be configured to be connected or linked by needles in an artificial arterio-venous graft (AVG) in, for example, the arm of a mannequin.

In an embodiment, the artificial arterio-venous graft (AVG) may be cannulatable and cannulated. The cannulatable AVG makes the apparatus similar to the actual renal dialysis real-world situations.

In an embodiment, the apparatus, the system, and/or tubing may be used to create an Arterio-Venous Fistula/Arterio-Venous Graft (AVF/AVG) configured to connect to a catheter.

In an embodiment, the arm graft may be connected to a catheter externally.

In an embodiment, the AVG may be configured to be connected or linked to an artificial heart in the mannequin's chest.

In an embodiment, the apparatus may offer the opportunity for training on inserting needles into the AVG/AVF. This is more realistic and mimics the real world, and the learner may encounter this during practice on actual patients.

In an embodiment, the access points or openings may be in the neck, chest, arm, axilla, abdomen, groin, and thigh. The mannequin may have at least one access point, for example, 2, 3, 4, 5, 6, 7, 8, 9, 10, or any combination thereof.

In an embodiment, the access points through the neck, chest, arm, axilla, abdomen, groin, thigh, etc., may serve the same or different (for example, hemodialysis and peritoneal dialysis) functions and may be linked to different structures. For example, access points in the neck, arm, and axilla, may have caps on the end of the Arterio-venous catheter/Arterio-venous fistula/Arterio-Venous Graft (AVG/AVF), which would require connection to bloodlines the same way that the heart catheter may connect. These may be a duplicate of the neck access, just using a different location. On the other hand, the access points in the abdomen and chest may be connected to the peritoneal bag and catheter.

In an embodiment, each access point may be of the same or different size. For example, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, any fraction thereof, etc., and any combination thereof.

In an embodiment, each access opening may have its bag, which may represent an artificial organ such as but not limited to the heart, kidney, peritoneal cavity, lungs, stomach, etc., and any combination thereof.

In an embodiment, the mannequin may have at least one bag, for example, 2, 3, 4, 5, 6, 7, 8, 9, 10, or any combination thereof.

In an embodiment, the bags may be made of permeable, semi-permeable, non-permeable materials, flexible, unbreakable, etc., and any combination thereof.

In an embodiment, the artificial organ is a vascular system further comprising silicone and natural rubber tubing 50A Durometer; 0.188 inch ID×0.313 inch OD (4.8 mm×8 mm).

In an embodiment, the internal vascular tubing may be 9-25 inches long, for example, 9, 9.5, 10, 10.5, 11, 11.5, 12, 12.5, 13, 13.5, 14, 14.5, 15, 15.5, 16, 16.5, 17.5, 18, 18.5, 19, 19.5, 20, 20.5, 21, 21.5, 22, 22.5, 23, 23.5, 24, 24.5, 25 inches, etc., and any combination thereof.

In an embodiment, the external catheter may be 4-21 inches in length, for example, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17.5, 18, 18.5, 19, 19.5, 20, 20.5 inches, etc.

In an embodiment, the internal diameter of the catheter may be 0.094 inch to 0.19 inches, for example, 0.095, 0.096, 0.097, 0.098, 0.099, 0.1, 0.12, 0.13, 0.14, 0.15, 0.16, 0.17, 0.185, 0.1875, 0.19, etc., and any combination thereof.

In an embodiment, the length of the bag may be up to 12 inches, for example, 3, 4, 5, 6, 7, 8, 8.5, 9, 9.5, 10, 10.5, 11, 11.5 inches; and the bag width from 4.5 to 5.5 inches, for example, 4.5, 4.75, 5, 5.25, 5.5, etc., and any combination thereof.

In an embodiment, catheter tubing connected to bag may be from 9-16 inches, for example 9.5, 10, 10.5, 11, 11.5, 12, 12.5, 13, 13.5, 14, 14.5, 15, 15.5, 16 inches, etc., and any combination thereof.

In an embodiment, the catheter attached to the venous port tubing at the Y connector may be from 3-20 inches, for example, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17.5, 18, 18.5, 19, 19.5, 20 inches, etc., and any combination thereof.

In an embodiment, the catheter attached to the arterial port tubing at the Y connector is 4-18 inches, for example, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17.5, 18, 18.5, 19, 19.5, 20 inches and any combination thereof.

In an embodiment, the venous port is represented by a blue cap on the end and the arterial port is represented by a red cap on the end of the port.

In an embodiment, the artificial organs and vascular system (bags and/or tubing) may be made of polyvinyl, natural, synthetic, rubber, Siliconized materials, silicone coated, silicone, latex rubber, polyvinyl chloride, PVC, silicone-Elastomer, etc., and any combination thereof.

In an embodiment, the artificial and vascular system (bags and/or tubing) may be made of plasticizers, Phthalate, Diisononyl Phthalate (DINP), Dioctyl Terephthalate (DOTP), Diisodecyl adipate (DIDA), Dioctyl adipate (DOA), Dioctyl sebacate (DOS), Trioctyl Trimellitate (TOTM), Epoxy fatty acid monoesters, diisononyl phthalate (DINP), diisodecyl phthalate (DIDP), etc., and any combinations thereof.

In an embodiment, the artificial organs and vascular system (bags and/or tubing) may be made of fire-retardants: Antimony trioxide (ATO), Decabromodiphenyl ethane, Tri (butoxyethyl) phosphate (TBEP), Zinc borate, etc., and any combination thereof.

In an embodiment, the artificial organs (bags and/or tubing) may be made of pigments such as Naphthol red 210, Titanium dioxide (TiO2), Zinc oxide (ZnO), Zinc sulfide (ZnS), etc., and any combination thereof.

In an embodiment, each access point may be connected to one or more tubing representing the vascular system.

In an embodiment, the artificial heart may be made up of a non-permeable bag.

In an embodiment, the artificial organs and vascular system (bags and/or tubing) may be made of synthetic materials, artificial, natural materials, or a combination thereof. Examples may be vinyl tubing, silicone, PVC tubing, natural latex rubber tubing, natural rubber tubing, self-sealing rubber tubing, siliconized materials, silicone coated, silicone, latex rubber, polyvinyl chloride or PVC, silicone-elastomer, etc., and any combination thereof.

In an embodiment, the artificial organs and vascular system (bags and/or tubing) may be collapsible. The collapsible bag may eliminate the accumulation of air pockets, allowing for continuous use and a more realistic experience.

In an embodiment, all maintenance may occur through the catheter.

In an embodiment, the internal simulated organs may be removed without destruction by draining the internal bags (artificial organs) through the catheter. Moreover, removing the grommets may allow for rotating the internal silicone bag through the opening without destruction.

In an embodiment, the artificial heart may contain and/or may be connected to a pressure-creating device, pump, liquid-moving device, or any combination thereof.

In an embodiment, the artificial heart may have a volume of 1, 2, 3, 4, 5, 6, 7, 8, 9 liters, or any fraction thereof.

In an embodiment, the artificial heart may be connected to a barbed Y-connector, wherein the female connector may be further connected to a dialysis bloodline.

In an embodiment, the artificial blood may be any variation of red color, such as but not limited to pure red, blood-colored, wine-colored, etc.

In an embodiment, the artificial blood may be any variation of dark red, bluish-red, purple, or blue color, such as but not limited to, venous blood-colored, etc.

In an embodiment, the artificial blood may be made up by adding a dye to the water. The concentration of the dye in the water may be up to 0.5%, 1%, 1.5%, 2%, 2.5%, 2.6, 2.7, 2.8, 2.9, 3%, 3.1%, 3.2%, 3.3%, 3.4%, 3.5%, 3.6%, 3.7%, 3.8%, 3.9%, 4%, 5%, etc., and any combination thereof. For example, 30 ml of liquid dye to 1 L bag, but the dye may be increased, decreased, and customized by the user based on their preferences and user visibility.

In an embodiment, the artificial blood may not leak or leak very little through the dialyzer.

In an embodiment, the artificial blood vessels may be self-sealing, leak-proof, leak-resistant, etc., or any combination thereof.

In an embodiment, the artificial skin may be self-sealing, leak-proof, leak-resistant, etc., or any combination thereof.

In an embodiment, the artificial organs represented by bag(s) may be self-sealing, leak-proof, leak-resistant, etc., or any combination thereof.

In an embodiment, the artificial organs represented by tubing(s) may be self-sealing, leak-proof, leak-resistant, etc., or any combination thereof.

In an embodiment, the looped graft may be from the arm or thigh, allowing for the insertion of dialysis needles and then connecting to a dialysis machine.

In an embodiment, the artificial organ is a cardiovascular system connected to an artificial arterio-venous graft by a barbed Y connector.

In an embodiment, at least one port on the artificial arterio-venous graft-Y connector is unclamped.

In an embodiment, the artificial organ is a cardiovascular system connected to a hemodialysis machine through a hemodialysis catheter port or an artificial arterio-venous graft by a barbed Y-connector.

In an embodiment, the artificial organ is a cardiovascular system, and the cardiovascular system is connected to an intravenous catheter configured to be renal dialyzed through the intravenous catheter.

In an embodiment, the graft loop may be up to 15 inches in length, for example, 5, 6, 7, 8, 9, 10, etc., and any combination thereof.

In an embodiment, the tubing attached to bag and y connector that connects to graft loop is up to 40 inches, for example, 30, 31, 32, 33, 34, 35, 36, 37, 38, 39, 40, inches and any combination thereof.

In an embodiment, an artificial arterio-venous graft barbed Y-connector color may be amber, red, clear, etc., and any combination thereof.

In an embodiment, an artificial arterio-venous graft barbed Y-connector may have an outer diameter of up to 11 mm. For example, 8, 8.5, 9, 9.5, 10, 10.5, 11 mm, etc., and any combination thereof.

In an embodiment, an artificial arterio-venous graft barbed Y-connector may have an inner diameter of up to 8 mm. For example, 5, 5.5, 6, 6.5, 7, 7.5, 8, mm, etc., and any combination thereof.

In an embodiment, the mannequin may lie down or supine as a patient does in real life.

In an embodiment, the mannequin may be upright, sitting, semi-supine, etc., and any combination thereof.

In an embodiment, the peritoneal dialysis bag holds 1-3 L liquid.

In an embodiment, the bag size is 5.25-15 inches wide, the bag height is 11-15 inches.

In an embodiment, the peritoneal tubing is 10-20 inches.

In an embodiment, the closed system is 20-30 inches in length.

In an embodiment, the end of the peritoneal dialysis catheter may have a transfer set attached to attach to peritoneal dialysis machine.

In an embodiment, the end of the peritoneal dialysis catheter is a female luer which can attach to the peritoneal dialysis machine.

In an embodiment, the shut-off mechanism applies mainly to the hemodialysis machine (may or may not apply to peritoneal dialysis). The dialysis machine may have a safety mechanism built inside to discern the presence of a blood leak. For example, a blood leak may occur when the dialyzer's membrane is damaged. In such a scenario, the blood may leak out through the membrane and enters the dialysis machine, where the blood may pass a sensor that may detect the presence of simulated blood. The blood leak detector may be bypassed to simulate dialysis entirely using simulated blood (with red dye). Otherwise, because the dye may diffuse through the dialyzer membrane, the machine may shut down, and the simulation of dialysis would not be able to take place.

A user or user's supervisor may bypass the blood leak detector. In addition, if the simulator (apparatus) uses water, the process may or may not be done without disarming the blood leak detector. This would not provide a realistic hemodialysis experience.

In an embodiment, an alarm, an alert may be sent to a trainee, instructor(s), etc., when there is a leak, no or low artificial blood.

In an embodiment, a sensor may detect no or low artificial blood in the apparatus, system, dialyzing machine, and/or any combination thereof.

In an embodiment, one or more sensors may be covered, uncovered, partially covered, etc., and the combination thereof with artificial blood. Alarms/alerts may be sent out when the sensor may be uncovered or partially covered with artificial blood.

In an embodiment, a leak in the apparatus, system, bags, tubing, and/or apparatus parts may set the alarm/alert system.

In an embodiment, a leak in the apparatus, system, and/or tubing may shut off, stop the system's functioning, apparatus, dialyzer machine, parts of the apparatus, etc., and any combination thereof.

In an embodiment, an alarm/alert may be sent to a trainee, instructor(s), etc., when there is a leak, no, or low artificial blood.

In an embodiment, the alarm/alert may be audio, visual, vibrational, etc., or any combination thereof.

In an embodiment, the alarm/alert may be local, short-, or long-distant, via wired, via wireless, to the dialyzing machine, a cellular phone, computer, and any other computerized machine.

In an embodiment, the leak may be detected by water/fluid sensing sensors placed in or around the tubing, bags, grafts, access point, in or outside of the mannequin limbs, torso, etc., and any combination thereof.

In an embodiment, the leak sensors may be connected to an alert/alarm system.

In an embodiment, the alert system may send out alerts/alarms locally, remotely, or both.

In an embodiment, the alerts may be sent to any internet-connected device.

In an embodiment, the alert system may be customizable.

In an embodiment, the alert may be sent in real-time or near real-time.

In an embodiment, the leak sensors may be connected to a shut-off mechanism.

In an embodiment, the artificial blood leakage may shut off the dialyzing machine.

In an embodiment, disarming the blood leak detection system may shut off the entire apparatus and system.

In an embodiment, the artificial blood may flow up to 50, 10, 150, 200, 250, 300, 350, 400 ml/min, or any fraction thereof.

In an embodiment, the apparatus and systems may be utilized for 1, 2, 3, 4, 5, 6, 7, 8, 9, 10, 12, 13, 14, 15, 20, 25, 30, 40, 50, 60, 70, 80, 90 hours, or any combination thereof.

In an embodiment, the ultrafiltration may be 100, 150, 200, 250, 300,350, 400, 450, 500, 750, 1000 milliliters, or any combination thereof.

In an embodiment, the apparatus may be used for longer times, simulating the real-life variations of dialysis requiring a longer period, more than 4 hours, for patients unable to tolerate standard hemodialysis. This allows for educating the user on the differences.

In an embodiment, connecting the AVG to the heart catheter may give the trainee the option of training using the AVG, and catheter individually or together.

In an embodiment, the catheter may be configured to be connected or linked to an artificial heart in the mannequin's chest.

In an embodiment, an artificial heart may be made of collapsible materials such as but not limited to polypropylene-polyethylene bland, synthetic materials, natural materials, etc., or any combination thereof. The collapsible bag eliminates the accumulation of air pockets, allowing for a more realistic experience.

In an embodiment, the artificial heart may cause no, low air in the dialysis machine, which may prevent a need for replacement of the system or part thereof, or a combination of both.

In an embodiment, the apparatus, the system, and/or tubing may be configured to be connected or linked to an artificial peritoneal cavity.

In an embodiment, the artificial peritoneal may be made of collapsible materials such as but not limited to polypropylene-polyethylene bland, synthetic materials, natural materials, etc., or any combination thereof.

In an embodiment, the artificial peritoneal cavity may cause no, low air in the dialysis machine, which may prevent a need for replacement of the apparatus, system, part thereof, or a combination thereof.

In an embodiment, the artificial peritoneal cavity may be a collapsible bag that allows for complete emptying of the bag without causing air to enter the peritoneal dialysis cycler. This collapsible bag may later be refilled with a dialyzing solution. The collapsible bag eliminates the accumulation of air pockets, allowing for use with the continuous peritoneal dialysis cycler.

In an embodiment, the artificial peritoneal cavity may be non-permeable, leak-proof, etc., or a combination thereof.

In an embodiment, a leak in the apparatus, system, and/or tubing may be detected by sensors.

In an embodiment, a leak in the device may be evidenced by fluid leaking from the joining parts of the mannequin or discoloration of the mannequin body from absorbing the dye.

In an embodiment, a leak in the tubing may cause a decrease in the venous and/or arterial pressure monitored by the venous and arterial transducers.

In an embodiment, the apparatus, system, and methods may be used in clinical, educational, home, etc., settings, or any combination thereof.

In an embodiment, the connecting of the AVG to the heart catheter gives the trainee the option of training using at least one of the AVG, catheter, or both.

In an embodiment, the catheter and the AVG could be connected within the apparatus and system independently of each other or without the need for each other.

In an embodiment, the catheter and the AVG could be connected within the apparatus and system dependently.

In an embodiment, a separate closed connection from the AVG to the artificial heart may prevent the need to connect the AVG to the catheter when simulation using the AVG is needed.

In an embodiment, the closed-loop dialyzing system may be used with or without a catheter. For example, the artificial blood vessels from the machine into the artificial heart may be coupled to a catheter depicting patients with a heart catheter or directly without a catheter depicting patients without a catheter.

In an embodiment, the artificial blood vessels and/or other tubing may be made of a self-sealing material, for example, natural rubber, synthetic material, etc.

In an embodiment, the artificial blood vessels and/or another tubing may be made to seal using a sealant, glue, etc. The seal may be airtight.

In an embodiment, artificial blood vessels and/or other tubing may be self-sealing, flexible, unbreakable, etc., and any combination thereof.

In an embodiment, the artificial blood vessels, catheter, and/or other tubing may be made of plasticizers, Phthalate, Diisonony Phthalate (DINP), Dioctyl Terephthalate (DOTP), Diisodecyl adipate (DIDA), Dioctyl adipate (DOA), Dioctyl sebacate (DOS), Trioctyl Trimellitate (TOTM), Epoxy fatty acid monoesters, diisononyl phthalate (DINP), diisodecyl phthalate (DIDP), etc., and any combinations thereof.

In an embodiment, the artificial blood vessels, tubing, catheter, etc., may be made of fire-retardants such as Antimony trioxide (ATO), Decabromodiphenyl ethane, Tri (butoxyethyl) phosphate (TBEP), Zinc borate, etc., and any combination thereof.

In an embodiment, the artificial blood vessels tubing, catheter, etc., may be made of pigments such as Naphthol red 210, Titanium dioxide ($TiO2$), Zinc oxide (ZnO), Zinc sulfide (ZnS), etc., and any combination thereof.

In an embodiment, each access point may be connected to one or more tubing representing the vascular system.

In an embodiment, the sealing and/or self-sealing materials may seal up to 10, 20, 30, 40, 50, 60, 70, 80, 90, 100, 110, 120, etc., times without any opening or holes in the tubing. These holes may or may not be at precisely the same location.

In an embodiment, the location of cannulation may be rotated to preserve the integrity of the self-sealing material.

In an embodiment, the cannulation may follow the process in the real world when cannulating a AVG or AVF. The site may be rotated so as not to traumatize the fistula or cause destruction of the graft material.

In an embodiment, the needle cannulations may be done up to 10, 20, 30, 40, 50, 60, 70, 80, 90, 100, 110, 120, etc., times without any breakage.

In an embodiment, the cannulating needle gauge size may be 14, 15, 16, 17 gauge, etc., or any fraction thereof.

In an embodiment, the cannulating needle may be 1 to 1.5 inches long.

In an embodiment, the total length of the needle and tubing from the needle tip to the connection hub is 14.5 to 16.5 inches, for example, 14.5, 15, 15.5, 16, 16.5 inches, and any fraction thereof.

In an embodiment, the dialysis simulation may be using the mannequin's arm, abdominal cavity, legs, wrist, hands, etc., or any combination thereof.

In an embodiment, the dialysis simulation may be done many times (e.g., up to 10, 20, 30, 40, 50, 60, 70, 80, 90, 100, 110, 120, etc.) before the replacement of the mannequin's artificial skin, artificial blood vessels, another tubing, etc., or any combination thereof.

In an embodiment, sealing and/or self-sealing materials may seal up to 10, 20, 30, 40, 50, 60, 70, 80, 90, 100, 110, 120, etc., times without any opening or holes.

In an embodiment, the mannequin may be at least partially hollow, for example 5%, 10%, 15%, 20%, 25%, 30%, 35%, 40%, 45%, 50%, 55%, 60%, 65%, 70%, 75%, 80%, 85%, 90 percent hollow of the total internal volume.

In an embodiment, the fully simulates a hemodialysis session with blood flow QBs up to 500 ml/min and treatment time up to 8 hours.

In an embodiment, the fully simulated peritoneal dialysis session takes up to 15 hours, for example, 1, 2, 3, 4, 5,6, 7, 8, 9, 10, 11, 12, 13, 14, 15 hours, etc., and any combination thereof.

In an embodiment, the peritoneal dialysis simulated on the cycler is usually up to 14 hours which occurs during sleeping hours, for example, 6, 7, 8, 9, 10, 11, 12, 13, 14 hours, etc., or any fraction thereof.

In an embodiment, continuous ambulatory peritoneal dialysis (CARD) which is manually is usually completed in cycles of up to 24 hour period continuously, for example, 15, 16, 17, 18, 19, 20, 21, 22, 23, 24 hours, and fraction thereof.

In an embodiment, the mannequin cavity may be filled with artificial organs, sensors, electronics, computer parts, batteries, pumps, etc., and any combination thereof.

In an embodiment, the mannequin cavity may be filled with filler materials to make the mannequin provide a realistic experience for the user. The filler materials may mimic subcutaneous fat, tissues, and organs for a realistic experience.

In an embodiment, the filler materials may be artificial, synthetic, natural materials, or any combination thereof.

In an embodiment, the mannequin represents the entire human body from the top of the head to the end of the feet.

In an embodiment, the mannequin may represent a part of the human body, such as the upper body, torso, etc., or any combination thereof.

In an embodiment, the mannequin may represent a part of the human body, such as lacking legs, thighs, any part of the legs, head, etc., and any combination thereof.

In an embodiment, the limbs, head, torso, artificial organs and parts thereof of the mannequin, and artificial organs may be attachable, detachable, detachably attached, or any combination thereof.

In an embodiment, the groin or thigh may be used as the $3^{rd}$ access point to make up the 3-in-1 simulator, and in this case, an entire or full-body mannequin may be used.

In an embodiment, the neck, axilla, arms, or any other upper body access point may be used for a 3-in-1 simulator, and in this case, a partial mannequin may be used, i.e., with torso but lacking legs, thighs, etc.

In an embodiment, the mannequin may be in appearance similar to a human female, human male, or both.

In an embodiment, the height of female mannequin may be up to 72 inches, for example, 20, 25, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 67, 68, 69, 70, 71, 72 inches, or any combination thereof.

In an embodiment, the male/female mannequin may be up to 6 feet, for example, 4, 5, 5.5, 6, 6.5, 7, 7.5, 8, 8.5, 9, feet, and any combination thereof.

In an embodiment, width of female mannequin (shoulder to shoulder) may be 10, 11, 12, 13, 14, 15, 16, 17, 18, 19, 20, 21, 22, 23, 24, 25, 26, 27, 28, 29, 30, inches etc., or any combination thereof.

In an embodiment, the depth of the female mannequin may be 5, 6, 7, 8, 9, 10, 11, 12, 13, 14, 15 inches, etc., and any combination thereof.

In an embodiment, the weight of a female mannequin may be 4, 4.5, 4.9, 5, 5.1, 5.2, 5.3, 5.4, 5.5, 5.6, 5.7, 5.8, 5.9, 6, 6.5, 7 pounds (lbs), etc., and any combination thereof.

In an embodiment, the height of male mannequin may be up to 72 inches, for example, 20, 25, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 67, 68, 69, 70, 71, 72 inches, or any combination thereof"

In an embodiment, the width of male mannequin (shoulder to shoulder): 15, 16, 17, 18, 19, 20, 21, 22, 23, 24, 25, 26, 27, 28, 29, 30, 31, 32, 33, 34, 35, inches, etc., and any combination thereof.

In an embodiment, the depth of a male mannequin may be 4, 5, 6, 7, 8, 9, 10, 11, 12, 13, 14, 15 inches, etc., and any combination thereof.

In an embodiment, the weight of a male mannequin may be 4, 4.5, 4.9, 5, 5.1, 5.2, 5.3, 5.4, 5.5, 5.6, 5.7, 5.8, 5.9, 6, 6.5, 7.1, 7.2, 7.3, 7.4, 7.5, 7.6, 7.7, 7.8, 7.9, 8, 8.1, 8.5 lbs., etc., and any combination thereof.

In an embodiment, male/female mannequins may come in various colors, for example, light tan, tan, medium tan, dark tan, brown, medium brown, dark brown, dark chocolate, etc., and any combination thereof.

In an embodiment, the mannequin may be made of polypropylene-polyethylene bland, plastic, soft-plastic, synthetic materials, natural materials, Siliconized materials, silicone coated, silicone, latex rubber, polyvinyl chloride or PVC, silicone-Elastomer, etc., and any combination thereof.

In an embodiment, the catheter, catheter/AVG may be made of Siliconized materials, silicone coated, silicone, latex rubber, polyvinyl chloride or PVC, silicone-Elastomer, etc., and any combination thereof.

The apparatus and system of the disclosure may be used in one or more methods. For example, the bags may be filled with water or another liquid with or without color dyes. The bags may be connected to a catheter, a cannulatable tubing, etc., and any combination thereof. The catheter or tubing may be connected to a dialysis machine for the dialysis to occur. The bags may be placed through the access point at at least one location, for example, 1, 2, 3, 4, 5, 6, 7, 8, etc., locations. The access point location may determine the dialysis type and method of performing the dialysis.

In an embodiment, the opening may allow for hemodialysis using a dialysis catheter attached to a bag.

In an embodiment, the chest opening may allow for hemodialysis using a dialysis catheter attached to a bag.

In an embodiment, the arm opening may allow for hemodialysis using an artificial Arterio-Venous Graft which is cannulated using dialysis needles.

In an embodiment, the groin opening allows for hemodialysis using a dialysis catheter attached to a bag.

In an embodiment, the thigh opening may allow for hemodialysis using a dialysis catheter attached to a bag or insertion of an artificial Arterio-Venous Graft which is cannulated using dialysis needles.

In an embodiment, the abdominal/belly opening may allow for peritoneal dialysis using a catheter attached to a bag.

In an embodiment, the bags, when filled with water and dye and placed in an appropriate location with appropriate connections, may become immediately ready for use. The locations and connections as detailed elsewhere in the disclosure.

In an embodiment, trainee caretakers and providers may use the system and apparatus to obtain blood cultures, draw blood specimens, intravenous infusions, administer blood transfusions, administer intravenous medications, etc., or any combination thereof.

Method of use of the apparatus, system of the disclosure, after unpacking the simulator, the mannequin may be sat in an upright position (this may facilitate the expansion of the bag and allow for filling from the bottom up). Next, attach secondary IV tubing to a water-filled bag (for example, 1-3 Liter). The water bag may connect to the hemodialysis catheter port, peritoneal dialysis catheter port, or AVG barbed Y-connector. One or both ports on AVG or peritoneal dialysis catheter may be unclamped. Fill one or more bags with simulated blood (for example, water) until water spills from an additional port. This may ensure the bag(s) may be completely filled and eliminates air pockets. The dye may be added (for example, 30 ml of liquid red dye to 1000 ml of water) to simulate blood. The simulator may be ready for use for the simulation training dialysis session. The user may enable or disable the blood leak detector.

In an embodiment, the peritoneal dialysis may involve a catheter that carries the dialysate in and out of the mannequin's abdomen. The tube may be inserted near the mannequin's belly button, chest area, or both. During continuous ambulatory peritoneal dialysis (CAPD), the mannequin's abdominal or peritoneal bag may be filled with dialysate. The dialysate may remain in the bag for a prescribed dwell time. Then the fluid may be drained. Gravity may move the fluid through the catheter and into and out of your abdomen.

In an embodiment, automated peritoneal dialysis (APD) may use the mannequin's abdominal or peritoneal bags, which may be connected to a machine (automated cycler) that may perform multiple exchanges. The cycler automatically fills the abdominal or peritoneal bag with dialysate, allows it to dwell there, and then drains it into a sterile bag that the trainee may empty.

In an embodiment, the limbs, head, torso, artificial organs, and parts thereof may be detachable, attachable, and may become engaged or assembled and disengaged or disassembled by turning or manipulating the mannequin or parts thereof.

In an embodiment, the mannequin simulator may be disassembled or assembled. This may be done by lining up the connection point(s), pulling down to engage, rotating the arm to engage, or both. The head may be rotated and removed. The head may be replaced by lining up the opening over the mount and pushing it down.

In an embodiment, the bag(s) may be drained by simply removing the caps from the catheter or disconnecting the AVG tubing from one end of the barbed connector. After drainage, the caps may be replaced, and AVG re-attached. The draining may be facilitated by tilting the mannequin from side to side, or by placing the mannequin in a Trendelenburg position.

In an embodiment, the bags may be drained by removing the caps of the catheters or disconnecting the AVG tubing from one end of the barbed connectors. Connect the tubing to the hemodialysis catheter/AVG. Open the clamp and drain into a container such as a bucket, sink, etc. The mannequin may be tilted from side to side as needed to drain the simulated blood, and the mannequin may be needed to place in the Trendelenburg position to bring fluid to the top.

In an embodiment, the bags may be drained at the end of the hemodialysis session by disconnecting the venous line and may be placed in a container such as a sink, large bucket, etc. The blood pump may be started and drained in the bags until air appears in the catheter line.

In an embodiment, the peritoneal dialysis catheter may be drained by connecting to a drainage bag and drain. The simulator, mannequin, catheter, and parts thereof may be turned from side to side as needed to drain fully In an embodiment, the mannequin or parts thereof may be cleaned by the use of a soft, damp cloth to wipe down the simulator when needed. Chemicals may not be used. Staining by the artificial blood may be prevented by placing an additional preventive layer underneath catheter opening when connecting and disconnecting.

In an embodiment, the bags and tubing may be cleaned periodically by filling them with a solution containing disinfectant such as 1:100 bleach water mixture and allowing the disinfecting solution to sit for a period of time, for example, for 5, 10, 11, 12, 13, 14, 15, 20 minutes and then draining. Such cleaning may be scheduled every 0, 1, 2, 3, 4, 5, 6, 7, 8, 9, 10, 11, 12, 13, 14, 15 days of use, etc., or any combination thereof.

In an embodiment, to prevent air in the tubing and bags, ensure that they may be completely full at the start of the training. Ultrafiltration UF may be set a goal of between 100-600 ml (additional volume may be required). If required, a large syringe may be used to remove trapped air pockets, and all connections may be secured to prevent air seepage.

In an embodiment, to prevent leakage in AVG, ensure tubing may be attached securely to a connector, advance needle to the hub, and tape securely. Rotate needle stick site and gauze may be placed and taped over leaky tubing during treatment. Change tubing may be required.

Example: A class often students may require hands-on training and learning of dialysis, both hemodialysis and peritoneal dialysis. Each student may get one or more training sections, which may be made of 5-8 hours. The apparatus may be set up as detailed before. Briefly, after unpacking the simulator, the mannequin may be upright (this may facilitate the expansion of the bag and allow for filling from the bottom up). Next, attach secondary IV tubing to a water-filled bag (for example, 1-3 Liter). The water bag may connect to the hemodialysis catheter port, peritoneal dialysis catheter port, or AVG barbed Y-connector. One or both ports on AVG or hemodialysis catheter may be unclamped. Fill one or more bags with simulated blood (for example, water) until water spills from an additional port. This may ensure the bag(s) may be completely filled and eliminates air pockets. The simulator may be ready for use for the simulation training dialysis session. The user may enable or disable the blood leak detector.

Each user may have their own bags, which they may test for the presence of a fluorescence dye. After each use, the apparatus may be drained and cleaned before another user may use it. The draining may be performed as follows: the bags may be drained by undoing caps. Connect the tubing to the hemodialysis catheter/AVG. Open the clamp and drain into a container such as a bucket, sink, etc. The mannequin may be tilted from side to side as needed to drain the simulated blood, and the mannequin may be required to place in the Trendelenburg position to bring fluid to the top. The cleaning may be done using a soft cloth, soap, and water.

DETAILED FIGURE DESCRIPTION

FIG. 1: Show here a simulated heart with blood vessels connected to a simulated artificial arterio-venous graft AV graft. The saline bag is 1.3 liter [101] and is connected to tubing, a blood vessel simulating artery and vein, [103] through a barbed y-connector that connects the graft to the blood vessel [104]. The bag may have one or two connectors [105], and one or both may be used. AV graft may be a requirement for hemodialysis. The loop AVG is represented by [102].

FIG. 2: Simulated heart with blood vessel connected to simulated dialysis catheter. The saline bag is the artificial heart [201] connected to vascular tubing [203] through spike [202] and barbed Y-connector [204], one or two connectors [206], and Barb Connector to Female Luer Lock [205].

FIG. 3: Shown here is a simulated peritoneal cavity and catheter. The saline bag is 1.3 liter is the artificial peritoneal cavity [301] is connected to tubing [303] through a spike [302], one or two connectors [305], and a Female Luer connector [304].

Figure 4:
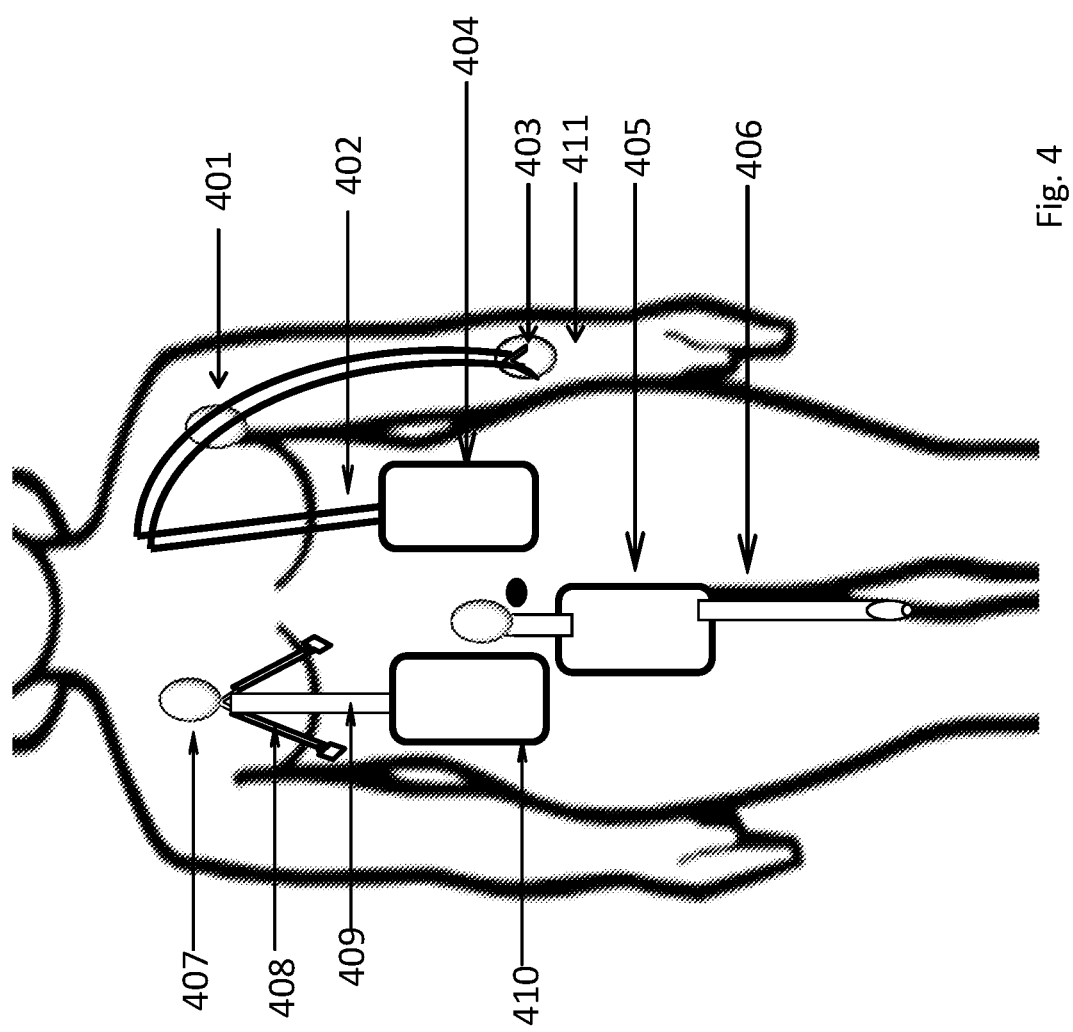
FIG. 4: Shown is the 3-in-1-simulator or dialyzing mannequin with catheter access, arterio-venous graft access, and peritoneal catheter access.

FIG. 4 shows the 3-in-1 simulator with catheter access, arterio-venous graft access, and peritoneal catheter access. Here are three different structural components and methods of performing dialysis, hemodialysis and peritoneal dialysis. The access opening in the arm and axilla is for inserting the artificial arterio-venous graft loop connected to an artificial heart [401, 403] via artificial blood vessels or tubing [402]. This model may perform at least 1, 2, 3, 4, 5, or any combination of different options for dialysis with one dialysis simulator apparatus and system. Hemodialysis may be performed using a dialysis catheter inserted into a central vein, an arterio-venous graft surgically implanted in the arm [403, 407], or performing peritoneal dialysis using a bag embedded inside the peritoneal cavity [404] of the mannequin. The artificial heart [402 or 410] inside the mannequin's chest is shown, which may be connected to the dialysis machine via bottom artificial heart ports linked to the machine tubing [401, 406, 408, 409]. The top of the artificial heart may be connected to an arterio-venous graft loop; the arterio-venous loop may be embedded inside the mannequin [401, 408, 409]. The loop graft [411] may be connected externally to a blood vessel simulating the artery and vein of FIG. 1, [103], through a barbed y-connector that connects the graft to the blood vessel of FIG. 1, [104], and may be accessed using arterio-venous fistula needless [401]. The first needle may be inserted on the right side of the loop graft, and a second needle may be inserted on the left side of the loop graft. The first needle may be inserted on the arterial side, which may be on the right or the left. This is determined by which artery the surgeon may use to attach the graft surgically. Therefore, the first needle (Arterial) may be inserted on the right or left side, with the second needle (venous) may be inserted on the opposite side of the first needle. The apparatus and system may also use the artificial peritoneal cavity with external access for dialysis and may have one or more access port(s) [404, 405, 406]. The peritoneal catheter may have only one access port coming from the peritoneal cavity [404]. The tubing that connects to the catheter may have many access ports depending upon the prescription; however, this may be separate and apart from the actual access that may be housed inside the mannequin's body. The artificial peritoneal cavity may be a collapsible bag [404]. The collapsible bag eliminates the accumulation of air, allowing for use with the continuous peritoneal dialysis cycler, and provides the user a more realistic experience.

Figure 5:
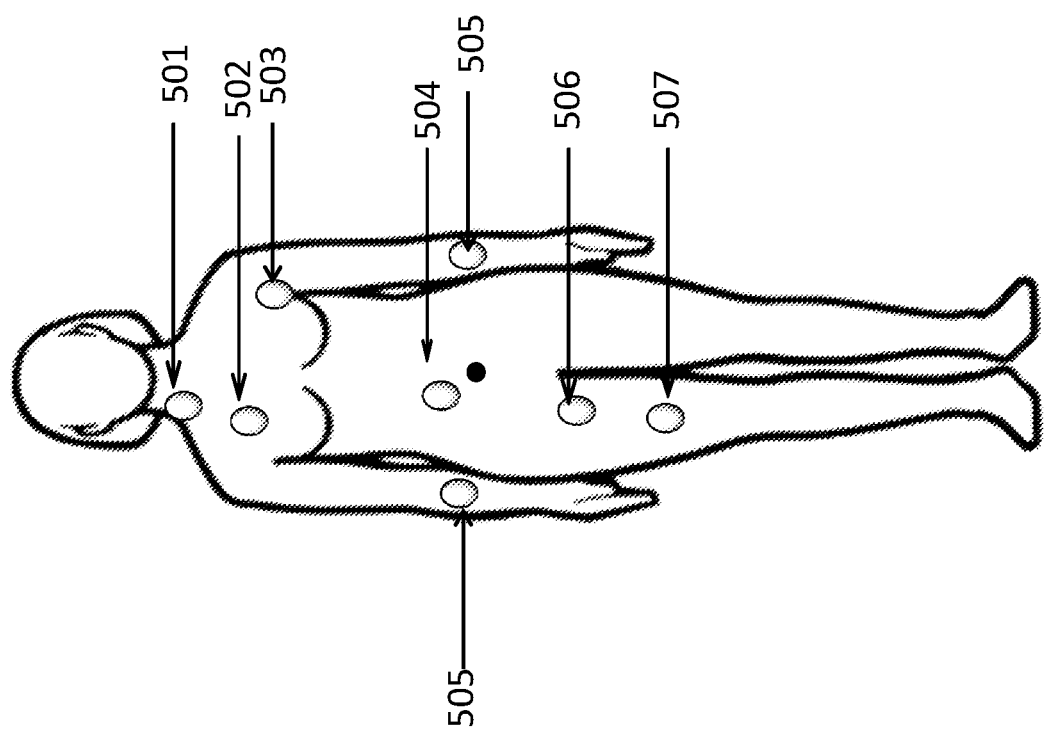
FIG. 5: Shown are access openings in the apparatus and system of this disclosure.

FIG. 5 shows access openings in the apparatus, wherein one or more access openings may be utilized for at least one dialysis function and machine. The access points through the neck [501], chest [502], arm [505], axilla [503], abdomen [504] that may not be the belly button but on the right or left of the belly button, groin [506], and thigh [507]. The opening at 506 and 507 may be on the right side of the body. One or more of these access openings may be used to insert various artificial organs, as detailed in previous figures and other components of this disclosure.

It is to be understood that the above description is intended to be illustrative and not restrictive. For example, the above-described embodiments (and/or aspects thereof) may be used in combination with each other. In addition, many modifications may be made to adapt a particular situation, method, system device or material to the teachings of the various embodiments of the invention without departing from their scope. While the particulars and details described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims and may include other examples that occur to those skilled in the art. Such other examples are intended to be within the scope of the claims if the examples have structural elements or steps that do not differ from the literal language of the claims or if the examples include equivalent structural elements or steps with insubstantial differences from the literal language of the claim.

I claim:

1. A renal dialysis training apparatus comprising at least one artificial organ system within a mannequin, wherein the mannequin is connected to two renal dialysis machines, wherein the first renal dialysis machine is a peritoneal dialysis machine and the second renal dialysis machine is a hemodialysis machine, wherein the at least one artificial organ system forms a closed-loop structure, the at least one artificial organ system is configured to be catheterized from outside at at least one location on the mannequin, and wherein the apparatus is configured for renal dialysis for a realistic user experience for the two renal dialyzing machines.

2. The apparatus of claim 1, wherein the at least one artificial organ is a peritoneal cavity comprising of flexible and collapsible bag configured to make the closed-loop structure pair-pocket free.

3. The apparatus of claim 1, wherein the renal dialysis is through catheter access, arterio-venous graft access, and peritoneal catheter access.

4. The apparatus of claim 1, wherein the at least one artificial organ is a cardiovascular system further connected to a hemodialysis catheter with two ports.

5. The apparatus of claim 1, wherein the at least one artificial organ is a cardiovascular system connected to an artificial arterio-venous graft barbed Y-connector.

6. The apparatus of claim 1, wherein the at least one artificial organ is a cardiovascular system connected to a hemodialysis machine through a hemodialysis catheter two-port.

7. The apparatus of claim 1, wherein the at least one artificial organ is a cardiovascular system connected to a hemodialysis machine through an artificial arterio-venous graft barbed Y-connector.

8. The apparatus of claim 1, wherein the at least one artificial organ is a cardiovascular system, and the cardiovascular system is connected to an intravenous catheter configured to be renal dialyzed through the intravenous catheter.

9. The apparatus of claim 1, wherein the at least one artificial organ is a cardiovascular system, and the cardiovascular system is connected to an arteriovenous fistula configured to be renal dialyzed through the arteriovenous fistula.

10. The apparatus of claim 1, wherein the at least one artificial organ is a peritoneal cavity connected to a peritoneal dialysis catheter port.

11. The apparatus of claim 1, wherein the dialysis is through a peritoneal cavity, wherein the peritoneal cavity is connected to a renal dialyzing machine.

12. The apparatus of claim 1, wherein the renal dialysis is a continuous cyclic peritoneal dialysis.

13. The apparatus of claim 1, wherein the renal dialysis is a continuous ambulatory peritoneal dialysis.

14. The apparatus of claim 1, wherein the catheterized outside location on the mannequin is self-sealing.

15. The apparatus of claim 1, wherein the at least one artificial organ is a cardiovascular system and a peritoneal cavity, wherein the cardiovascular system and peritoneal cavity comprise individual, separate, flexible, and collapsible bags.

16. The apparatus of claim 1, wherein the at least one artificial organ in the mannequin can be accessed through an opening selected from the group consisting of chest, arm, abdominal cavity, thigh, groin, neck, and any combination thereof.

17. The apparatus of claim 1, wherein the mannequin height is 39 to 72 inches, shoulder to shoulder width of 16 to 22 inches, depth of 7 to 10 inches, and weight of 5.4 lbs. to 7.6 lbs.

18. The apparatus of claim 1, wherein the closed-loop structure is connected to a liquid leak sensing alarm system of the dialysis machine.

19. The apparatus of claim 1, wherein the apparatus further comprises a safety shut-off system and mechanism.

20. The apparatus of claim 1, wherein the at least one artificial organ is a cardiovascular system further comprising an internal vascular tubing from 9 to 25 inches long, and a heart mimicking bag, wherein the heart mimicking bag length is up to 12 inches, and the heart mimicking bag width is from 4.5 to 5.5 inches; wherein the apparatus is configured for 10 hours use.

21. The apparatus of claim 1, wherein the renal dialysis is through an external catheter, wherein the renal dialyzes external catheter is from 4 to 18 inches in length, and an internal diameter of the catheter is from 0.094 inches to 0.1875 inches.

22. The apparatus of claim 1, where in the mannequin further comprising of limbs, head, torso, and the at least one artificial organ system, wherein the limbs, the head, the torso, and the at least one artificial organs are detachable and attachable.

23. The apparatus of claim 1, wherein the at least one artificial organ system is configured to be cannulated by a cannulating needle size is from 14 to 17 gauge.

24. The apparatus of claim 1, wherein the at least one artificial organs further comprising of at least one of the selected from a group consisting of plasticizers, Phthalate, Diisononyl Phthalate (DINP), Dioctyl Terephthalate (DOTP), Diisodecyl adipate (DIDA), Dioctyl adipate (DOA), Dioctylsebacate (DOS), Trioctyl Trimellitate (TOTM), Epoxy fatty acid monoesters, diisononylphthalate (DINP), diisodecyl phthalate (DIDP), silicon, natural rubber, Antimony trioxide(ATO), Decabromodiphenyl ethane, Tri (butoxyethyl) phosphate(TBEP), Zinc borate, vinyl tubing, silicone, PVC tubing, natural latex rubber tubing, natural rubber tubing, self-sealing rubber tubing, siliconized materials, silicone coated, silicone, latex rubber, polyvinylchloride or PVC, silicone-elastomer, and any combinations thereof.

25. The apparatus of claim 1, wherein the mannequin is configured for renal dialysis in a supine position.

* * * * *